US010564243B2

(12) United States Patent
Griswold et al.

(10) Patent No.: US 10,564,243 B2
(45) Date of Patent: Feb. 18, 2020

(54) SYSTEM AND METHOD FOR PHASE CYCLING MAGNETIC RESONANCE FINGERPRINTING (PHC-MRF)

(71) Applicant: Case Western Reserve University, Cleveland, OH (US)

(72) Inventors: Mark A. Griswold, Shaker Heights, OH (US); Bhairav Bipin Mehta, Cleveland, OH (US); Simone Coppo, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 95 days.

(21) Appl. No.: 15/944,637

(22) Filed: Apr. 3, 2018

(65) Prior Publication Data

US 2018/0292492 A1  Oct. 11, 2018

Related U.S. Application Data

(60) Provisional application No. 62/482,765, filed on Apr. 7, 2017.

(51) Int. Cl.
| | |
|---|---|
| *G01V 3/00* | (2006.01) |
| *G01R 33/561* | (2006.01) |
| *G01R 33/50* | (2006.01) |
| *G01R 33/56* | (2006.01) |
| *A61B 5/055* | (2006.01) |

(Continued)

(52) U.S. Cl.
CPC ............ *G01R 33/561* (2013.01); *A61B 5/055* (2013.01); *G01R 33/34092* (2013.01); *G01R 33/3808* (2013.01); *G01R 33/50* (2013.01); *G01R 33/5608* (2013.01)

(58) Field of Classification Search
CPC ..................................... G01R 33/561
USPC .................................. 324/307, 309
See application file for complete search history.

(56) References Cited

U.S. PATENT DOCUMENTS

| | | |
|---|---|---|
| 8,723,518 B2 | 5/2014 | Seiberlich et al. |
| 2015/0301141 A1 | 10/2015 | Griswold et al. |

(Continued)

OTHER PUBLICATIONS

Bangerter, et al., Analysis of Multiple-Acquisition SSFP, Magnetic Resonance in Medicine, 2004, 51:1038-1047.

(Continued)

*Primary Examiner* — Louis M Arana
(74) *Attorney, Agent, or Firm* — Quarles & Brady LLP (57) ABSTRACT

A system and method is provided for performing a magnetic resonance fingerprinting (MRF) study in the face of inhomogeneous magnetic fields. The process includes performing a balanced steady-state free precession (bSSFP) pulse sequence multiple times to acquire a multiple MRF datasets from at region of interest (ROI) in a subject, wherein performing the multiple bSSFP pulse sequences includes cycling through multiple phase patterns that differ across the multiple times. The process also includes comparing the multiple MRF datasets with a MRF dictionary to determine at least one tissue property indicated by each of the multiple MRF datasets, producing an aggregated indication of the at least one tissue property, and producing at least one map of the at least one tissue property using the aggregated indication of the at least one tissue property.

16 Claims, 6 Drawing Sheets

(51) Int. Cl.
*G01R 33/34* (2006.01)
*G01R 33/38* (2006.01)

(56) References Cited

U.S. PATENT DOCUMENTS

| 2015/0301147 | A1* | 10/2015 | Gulani | G01R 33/56563 |
| | | | | 324/309 |
| 2016/0116559 | A1* | 4/2016 | Cohen | G01R 33/561 |
| | | | | 324/309 |
| 2018/0203082 | A1* | 7/2018 | Griswold | G01R 33/5608 |
| 2018/0217220 | A1* | 8/2018 | Gulani | G01R 33/5659 |

OTHER PUBLICATIONS

Benkert, et al., Dynamically Phase-Cycled Radial Balanced SSFP Imaging for Efficient Banding Removal, Magnetic Resonance in Medicine, 2015, 73(1):182-194.

Bjork, et al., Parameter Estimation Approach to Banding Artifact Reduction in Balanced Steady-State Free Precession, Magnetic Resonance in Medicine, 2014, 72(3):880-892.

Christen, et al., MR Vascular Fingerprinting: A New Approach to Compute Cerebral Blood Volume, Mean Vessel Radius, and Oxygenation Maps in the Human Brain, NeuroImage, 2014, 89:262-270.

Christen, et al., MR Fingerprinting and B0 Inhomogeneities, Proc. Intl. Soc. Mag. Reson. Med., 2015, 23:3236.

Coppo, et al., Magnetic Resonance Fingerprinting Using Phase Cycling bSSFP (phc-MRF) in Presence of B0 Inhomogeneity, Proc. Intl. Soc. Mag. Reson. Med., 2017, 25:5060.

Jiang, et al., MR Fingerprinting Using Fast Imaging with Steady State Precession (FISP) with Spiral Readout, Magnetic Resonance in Medicine, 2015, 74(6):1621-1631.

Jiang, et al., Use of Pattern Recognition for Unaliasing Simultaneously Acquired Slices in Simultaneous Multislice MR Fingerprinting, Magnetic Resonance in Medicine, 2017, 78:1870-1876.

Keenan, et al., Comparison of T1 Measurement Using ISMRM/NIST System Phantom, in ISMRM 24th Annual Meeting, 2016, Program #3290, 24 pages.

Lee, et al., Fast 3D Imaging Using Variable-Density Spiral Trajectories With Applications to Limb Perfusion, Magnetic Resonance in Medicine, 2003, 50:1276-1285.

Ma, et al., Magnetic Resonance Fingerprinting, Nature, 2013, 495:187-192.

Pelot, et al., Quantification of Superparamagnetic Iron Oxide Using Inversion Recovery Balanced Steady-State Free Precession, Magnetic Resonance Imaging, 2013, 31:953-960.

Russek, et al., Characterization of NIST/ISMRM MRI System Phantom, Proc. Intl. Soc. Mag. Reson. Med., 2012, 20:2456.

Ye, et al., Accelerating Magnetic Resonance Fingerprinting (MRF) Using t-Blipped Simultaneous Multislice (SMS) Acquisition, Magnetic Resonance in Medicine, 2016, 75:2078-2085.

European Patent Office, Extended European Search Report, Application No. 18166020.0, dated Sep. 5, 2018, 9 pages.

* cited by examiner

SYSTEM AND METHOD FOR PHASE CYCLING MAGNETIC RESONANCE FINGERPRINTING (PHC-MRF)

CROSS-REFERENCE TO RELATED APPLICATIONS

This application is based on, claims priority to, and incorporates herein by reference in its entirety for all purposes, U.S. Provisional Application Ser. No. 62/482,765, filed Apr. 7, 2017, and entitled "SYSTEM AND METHOD FOR PHASE CYCLING MAGNETIC RESONANCE FINGERPRINTING (PHC-MRF)."

STATEMENT REGARDING FEDERALLY SPONSORED RESEARCH

This invention was made with Government support under contract EB016728 and contract EB017219 awarded by the National Institutes of Health. The Government has certain rights in the invention.

BACKGROUND

Characterizing tissue species using nuclear magnetic resonance ("NMR") can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting ("MRF"), which is described, as one example, by D. Ma, et al., in "Magnetic Resonance Fingerprinting," Nature, 2013; 495(7440): 187-192.

Conventional magnetic resonance imaging ("MRI") pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time ("TE"), while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When conventional magnetic resonance ("MR") images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration.

Unlike conventional MRI, MRF employs a series of varied sequence blocks that simultaneously produce different signal evolutions in different resonant species (e.g., tissues) to which the radio frequency ("RF") is applied. The signals from different resonant tissues will, however, be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions calculated from physical principles and/or previously acquired evolutions. A large set of known evolutions may be stored in a dictionary.

Thus, MRF provides a framework that combines the transient state of the signal evolution with dictionary matching to achieve accurate and efficient multi-parameter maps. The original MRF design was based on a balanced steady state (bSSFP) acquisition, which is sensitive to T1, T2 and off-resonance (B0), and provides high signal to noise ratio (SNR). The signal intensity is dependent on the off-resonance frequency, which allows B-field mapping, but can also lead to banding artifacts in cases of significant B-field variations. A SSFP-MRF approach was proposed to eliminate banding artifacts, but it presents lower SNR and lack of B-field sensitivity.

As such, a need persists to overcome these challenges with traditional MRF acquisitions.

SUMMARY OF THE DISCLOSURE

The present disclosure provides systems and methods for a balanced steady state free precession (bSSFP) based MRF framework, which allows for different phase cycling (phc-MRF). The phase cycling may be used to compensate for banding artifact induced by B0 inhomogeneity.

In accordance with one aspect of the disclosure, a method is provided for performing a magnetic resonance fingerprinting (MRF) study. The method includes performing a balanced steady-state free precession (bSSFP) pulse sequence multiple times to acquire a multiple MRF datasets from at region of interest (ROI) in a subject, wherein performing the multiple bSSFP pulse sequences includes cycling through multiple phase patterns that differ across the multiple times. The process also includes comparing the multiple MRF datasets with a MRF dictionary to determine at least one tissue property indicated by each of the multiple MRF datasets, producing an aggregated indication of the at least one tissue property, and producing at least one map of the at least one tissue property using the aggregated indication of the at least one tissue property.

In accordance with another aspect of the disclosure, a system is provided that includes a magnet system configured to generate a polarizing magnetic field about at least a portion of a subject and a magnetic gradient system including a plurality of magnetic gradient coils configured to apply at least one magnetic gradient field to the polarizing magnetic field. The system also includes a radio frequency (RF) system configured to apply an RF field to the subject and to receive magnetic resonance signals from the subject using a coil array and a computer system. The computer system is programmed to control the magnetic gradient system and the RF system to perform a balanced steady-state free precession (bSSFP) pulse sequence multiple times to acquire a multiple MRF datasets from at region of interest (ROI) in a subject, wherein performing the multiple bSSFP pulse sequences includes cycling through multiple phase patterns that differ across the multiple times. The computer system is also programmed to compare the multiple MRF datasets with a MRF dictionary to determine at least one tissue property indicated by each of the multiple MRF datasets, produce an aggregated indication of the at least one tissue property, and produce at least one map of the at least one tissue property using the aggregated indication of the at least one tissue property.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Magnetic resonance fingerprinting ("MRF") is a technique that facilitates mapping of tissue or other material properties based on random or pseudorandom measurements of the subject or object being imaged. In particular, MRF can be conceptualized as employing a series of varied "sequence blocks" of radio-frequency ("RF") pulses that produce different signal evolutions in different "resonant species" to which the RF pulses are applied. The term "resonant species," as used herein, refers to a material, such as water, fat, bone, muscle, soft tissue, and the like, that can be made to resonate using NMR. By way of illustration, when RF energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE"), sampling patterns, and the like, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, longitudinal relaxation time ($T_1$), transverse relaxation time ($T_2$), main or static magnetic field map ($B_0$), and proton density ($\rho$). MRF is generally described in "Magnetic Resonance Fingerprinting," Ma D et al., Nature 2013:495, (7440):187-192 and U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel can be estimated to be the values that provide the best signal matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \sum_{i=1}^{N_A} \sum_{j=1}^{N_{RF}} R_i(\alpha) R_{RF_{ij}}(\alpha, \phi) R(G) E_i(T_1, T_2, D) M_0; \quad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha, \phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1, T_2, D)$ is a signal decay due to relaxation differences; and $M_0$ is the magnetization in the default or natural alignment to which spins align when placed in the main magnetic field.

While $E_i(T_1, T_2, D)$ is provided as an example, in different situations, the decay term, $E_i(T_1, T_2, D)$, may also include additional terms, $E_i(T_1, T_2, D, K)$ or may include fewer terms, such as by not including the diffusion relaxation, as $E_i(T_1,T_2)$ or $E_i(T_1,T_2,K)$. Also, the summation on "j" could be replace by a product on "j".

The dictionary may store signals described by, $$S_i = R_i E_i(S_{i-1}) \qquad (2);$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

As described, MRF provides a framework for multiple tissue parameter mapping based on a single acquisition. This framework combines the transient state of the signal evolution with dictionary matching to achieve accurate and efficient multi-parameter maps. The original MRF design was based on a balanced steady state free precession (bSSFP) acquisition, which can be sensitive to T1, T2, and off-resonance (B0) and provide high signal to noise ratio (SNR). The signal intensity is dependent on the off-resonance frequency, which allows magnetic field mapping, but can also lead to banding artifacts in cases of significant magnetic field variations. A steady state free precession (SSFP)-MRF approach was proposed to eliminate banding artifacts, but it presents lower SNR and lack of magnetic field sensitivity. Thus, as will be described, the present disclosure presents an approach for MRF that is based on a bSSFP sequence, but that can control banding artifacts through cycling variation of the radiofrequency (RF) pulses phase (phc-MRF).

Figure 1:
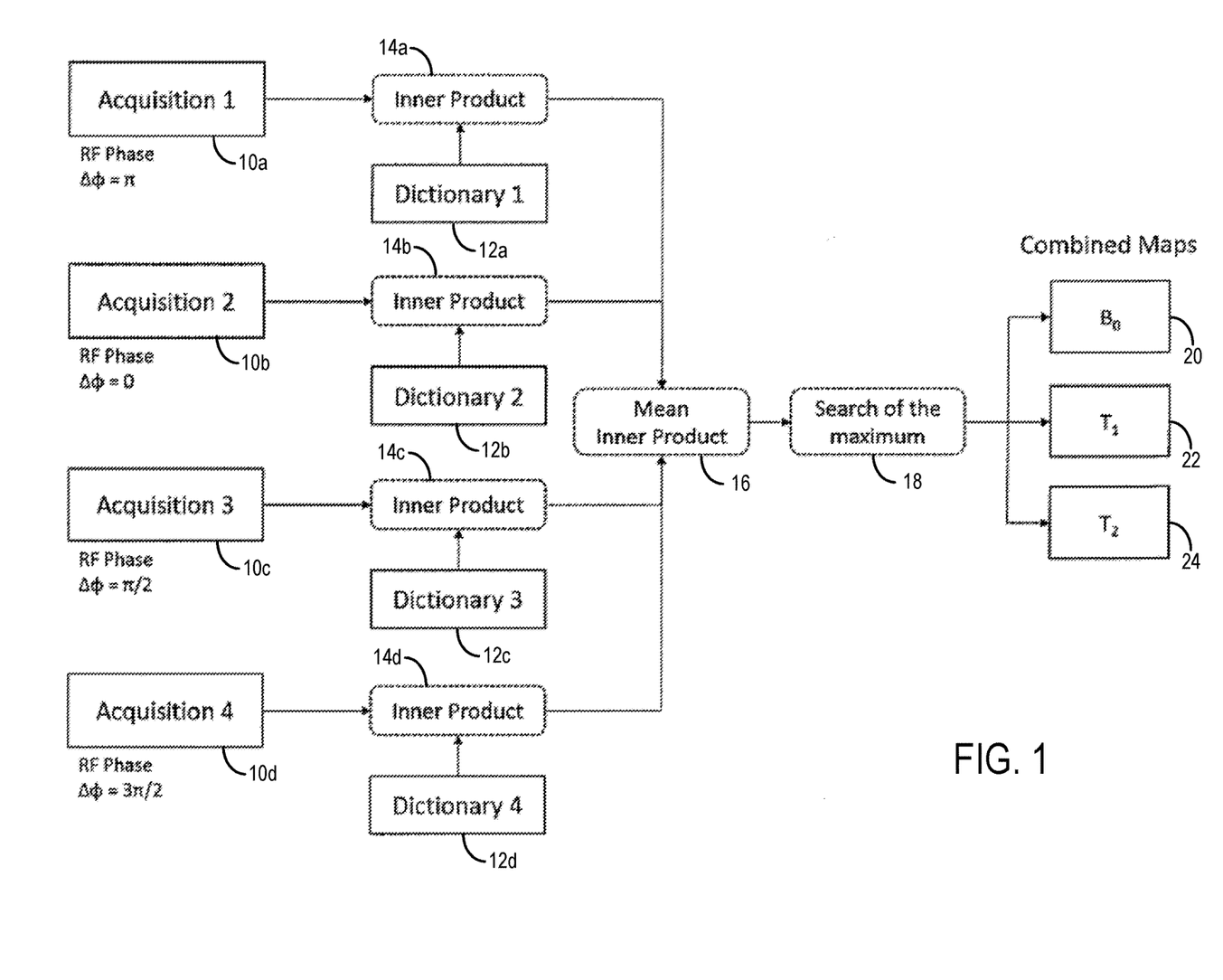
FIG. 1 is a schematic flow chart illustrating one, non-limiting example of a process in accordance with the present disclosure.

Referring to FIG. 1 a flowchart is provided for one implementation of a process in accordance with the present disclosure. To start, multiple phase-cycled bSSFP pulse sequence $10a$, $10b$, $10c$, $10d$ may be used to acquire MRF data one after each other. In this non-limiting example, four repetitions of the pulse sequence are illustrated but more or less repetitions may be desired. Each acquisition $10a$-$10d$ can use one arm of a variable density spiral trajectory for each TR to acquire an image (timepoint). For each of the may timepoints (e.g., 900 timepoints) used to acquire all desired MRF data, the RF excitation flip angle (FA), the repetition time (TR), the RF pulse phase, spiral arm orientation, or other parameters can be varied to, thereby, acquire signal evolutions forming MRF data.

Figure 2A:
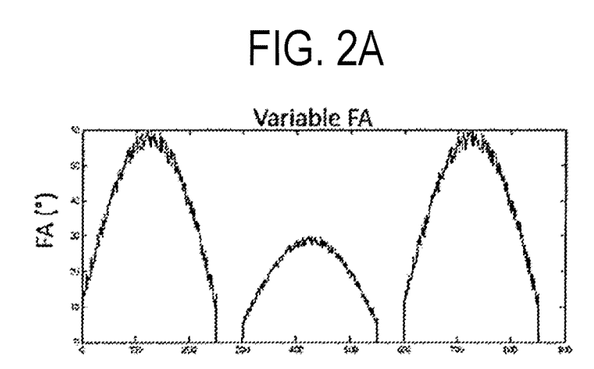
FIG. 2A is a graph of flip angles (FA) used in one non-limiting implementation of the process of FIG. 1.
Figure 2B:
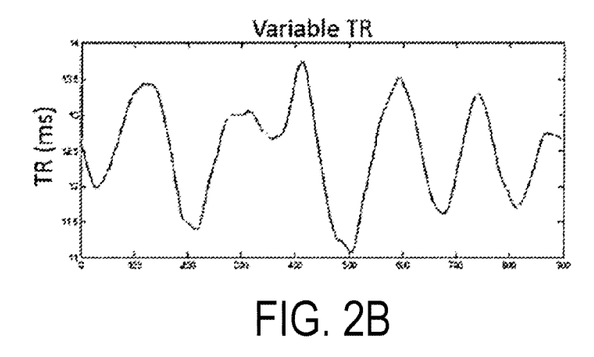
FIG. 2B is a graph of repetition time (TR) used in one non-limiting implementation of the process of FIG. 1.
Figure 2C:
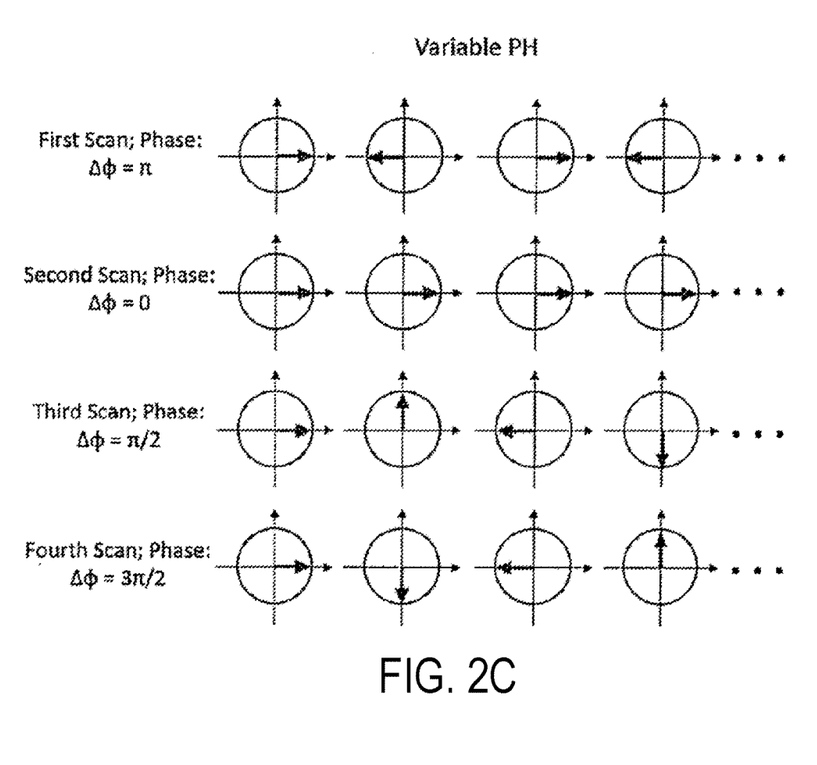
FIG. 2C is a schematic illustration of varied phases used in one non-limiting implementation of the process of FIG. 1.

In one non-limiting example, referring to FIGS. 2A and 2B, the four acquisitions can share the same FA and TR variations, as well as presenting an inversion pulse with, in this non-limiting example, a time of 20.64 ms prior to the acquisition. In this case, the RF pulse phase can change for each acquisition, as illustrated by the phase of the four initial pulses shown schematically in FIG. 2C. In this non-limiting example, the trajectory rotated 7.5° at each timepoint for all acquisitions Referring again to FIG. 1, the four acquisitions $10a$-$10d$ use a linear phase cycling with a phase increment ($\Delta\varphi$) for each timepoint of $\pi$, $0$, $\pi/2$ and $3\pi/2$ respectively. This phase increment, or offset, can have or form any of a variety of patterns. Four different dictionaries $12a$-$12d$ can be used for the four acquisitions $10a$-$10d$. Each voxel of a given MRF dataset acquired from a given acquisition $10a$-$10d$ can be matched with the respective dictionary $12a$-$12c$ through, as a non-limiting example, $L_2$-normalized matching, for example, an inner product (IP) $14a$-$14d$. Then, the matched values from all four matchings can be used to form an aggregated dataset. For example, the aggregated dataset can be formed by averaging the matches $14a$-$14d$ at process block 16 to select the atom providing the highest average match at process block 18 and estimate T1, T2, and B0 maps, 20, 22, 24. That is, one example of a matching can be performed by taking the inner product between the voxel signal and each dictionary and the entry in the dictionary that returns the highest value is considered to be the one that best represents the tissue properties, such that the respective T1, T2 and/or off-resonance values can be assigned to the voxel.

The $L_2$-normalized match values being averaged at process block 16, before looking for the highest value at process block 18, yields the dictionary atom representing each voxel. Though variations on this implementation may be performed, this particular, non-limiting implementation enforces the prior knowledge that the atom to be selected to be the same for all four scans. The dictionary atom providing the maximum average matching is selected to retrieve the T1, T2, and B0 map 20, 22, 204, of the relative voxel.

The above-described phc-MRF technique was tested on a healthy volunteer after informed consent in this IRB approved study and on an ISMRM/NIST MR system phantom. The acquisition were performed on a 3T system (Skyra, Siemens, Erlangen, Germany) and data were acquired with a 16 channel array. Images of 256×256 base resolution and 300 mm field of view were acquired. The volunteer acquisition was performed on a level of the brain close to the frontal sinus, where pronounced B0 inhomogeneity is present. The phantom acquisition was performed with a gradient applied along the x axis to generate a linearly varying frequency shift. The volunteer results were compared to the uncombined maps, while the phantom results were compared to the values provided by NIST.

Figure 3:
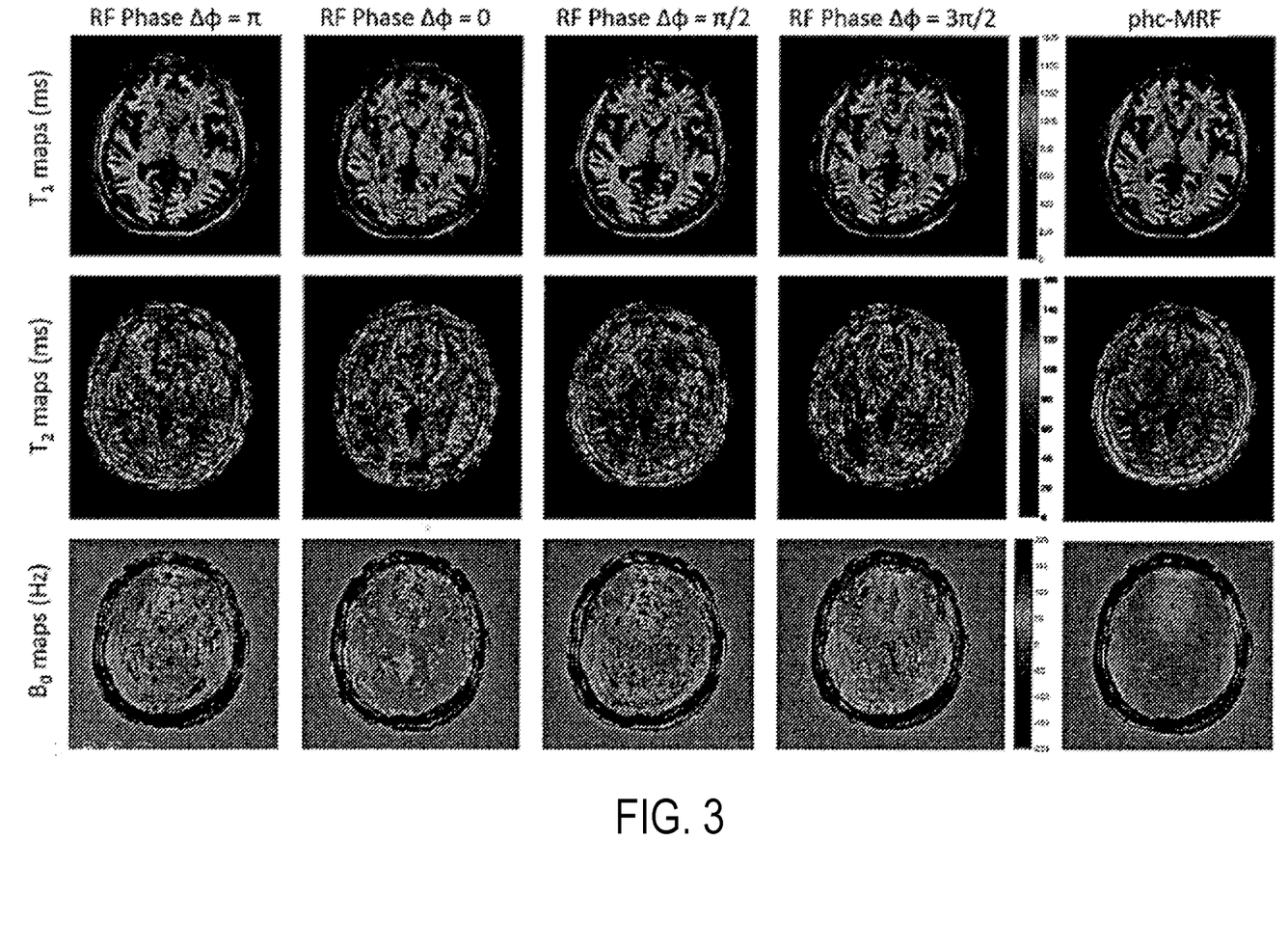
FIG. 3 is a set of images acquired from a subject illustrating the results of individual datasets and an aggregated dataset in accordance with the present disclosure.

The T1, T2, and B0 maps obtained from the volunteer using the above-described acquisition are shown in FIG. 3. Specifically, the T1 maps are provided on the top row, T2 maps in the middle row, and B0 maps on the bottom row. Each acquisition is reflected in the four columns, with the phc-MRF maps provide din the rightmost column. While each acquisition provides maps which are sub-optimal and presents banding artifacts, the combination of the four of them provides artifact-free maps through the entire FOV.

That is, from the B0 maps, one can notice the wide variation of off-resonance frequency due to the inhomogeneity induced by the tissue-air interface at the level of the sinus. Each of the single T1 maps presents artifacts in different region of the FOV, due to the different frequency response of each acquisition caused by the different RF pulses phase cycles. When combined in the reconstruction identified under the "phc-MRF" heading, nearly all banding artifacts are removed. The T2 maps of the individual acquisitions, instead, are of poor quality, due to the artifacts and the limited number of timepoints used for reconstruction. When the four acquisition are combined, though, good quality T2 maps are obtained.

Figure 4:
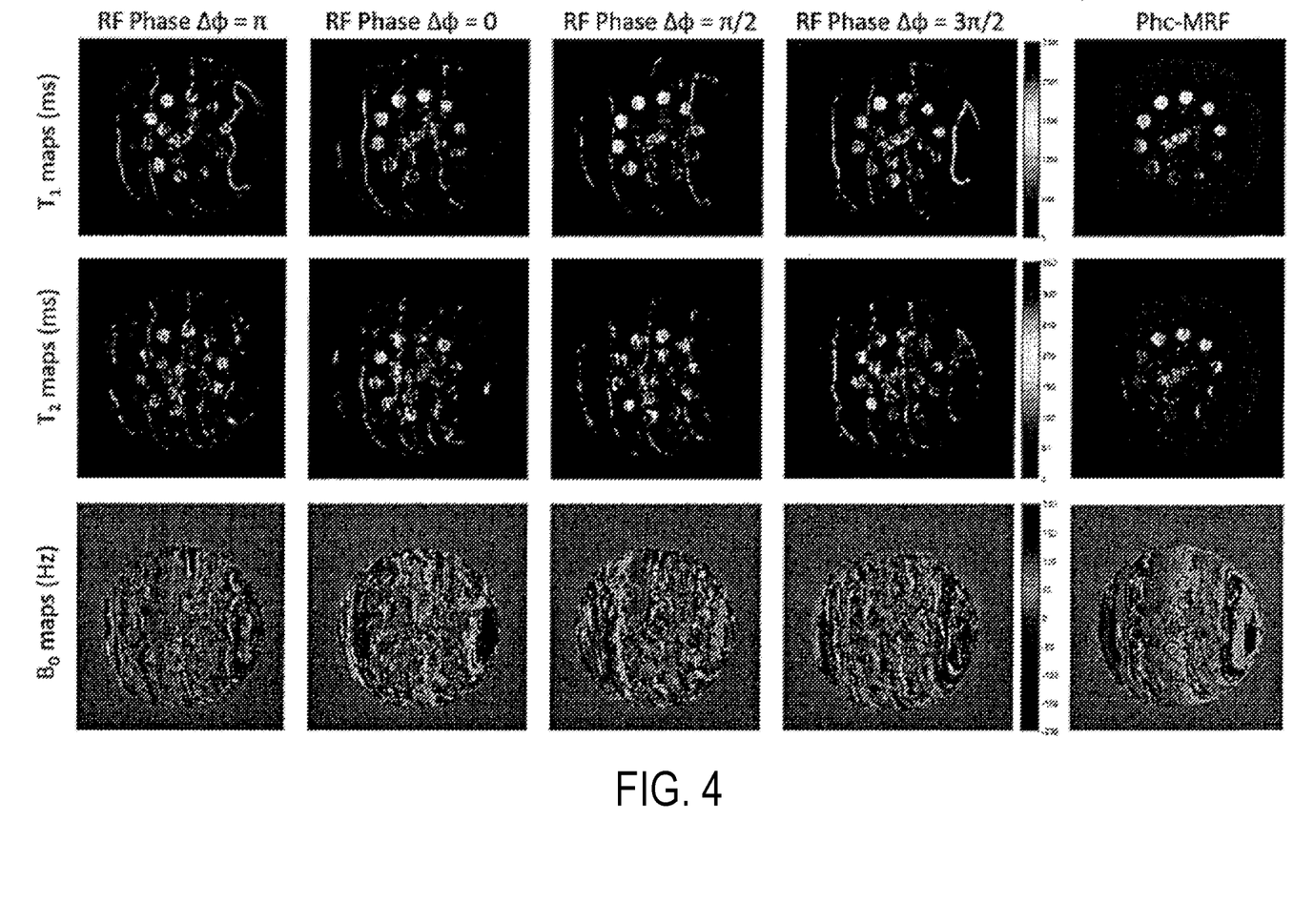
FIG. 4 is a set of images acquired from a phantom illustrating the results of individual datasets and an aggregated dataset in accordance with the present disclosure.
Figure 5A:
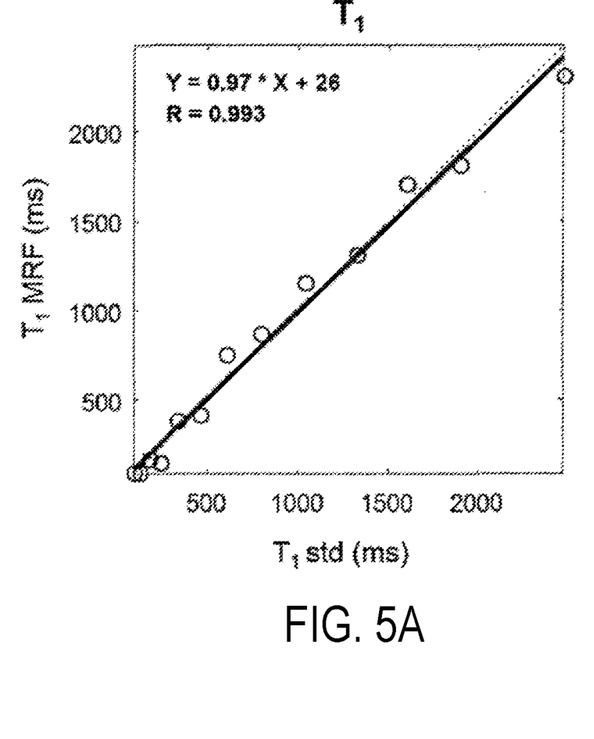
FIG. 5A is a graph of T1 measurements acquired in accordance with the present disclosure against standard T1 measurements.
Figure 5B:
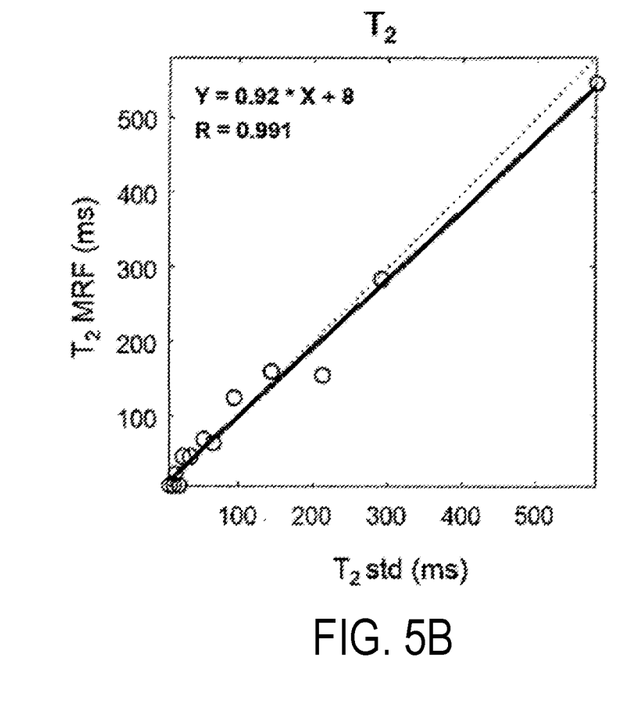
FIG. 5B is a graph of T2 measurements acquired in accordance with the present disclosure against standard T2 measurements.

The same maps obtained on the NIST phantom are shown in FIG. 4. The linear gradient along the X axis generated vertical banding artifacts, which are clearly visible in the four singular scans, while the combined phc-MRF T1 and T2 maps are artifact free. The B0 phc-MRF maps shows the linear increase of frequency along the field of view. Notably that the deionized water surrounding the spheres has parameters outside the physiological range, were this MRF framework was not optimized for, thus affecting the matching accuracy especially for the B0 map. The inhomogeneity induced by the gradient caused extensive artifacts which were compensated in the combined reconstruction which provided T1 and T2 values matching with the standard values within physiological range, which are illustrated in FIGS. 5A and 5B. That is, in FIGS. 5A and 5B, average T1 and T2 values measured in the 14 spheres of the phantom from the phc-MRF reconstruction are illustrated. Good agreement between the measured values and the NIST reference values were obtained within the physiological range (T1<1500 ms and T2<200 ms).

The results demonstrate that the MRF framework allows the combination of multiple different phase cycling to reduce the banding artifacts in a bSSFP-based acquisition. It is noted that each acquisition uses multiple timepoints that, collectively, may reach the total number of timepoints using in a standard acquisition originally (e.g., 900 timepoints per acquisition across multiple acquisitions versus 3000 timepoints in a traditional acquisition), such that the total scan time efficiency is minimally affected. It is also contemplated that the multiple (e.g., four) acquisitions may be merged in a single acquisition.

Figure 6:
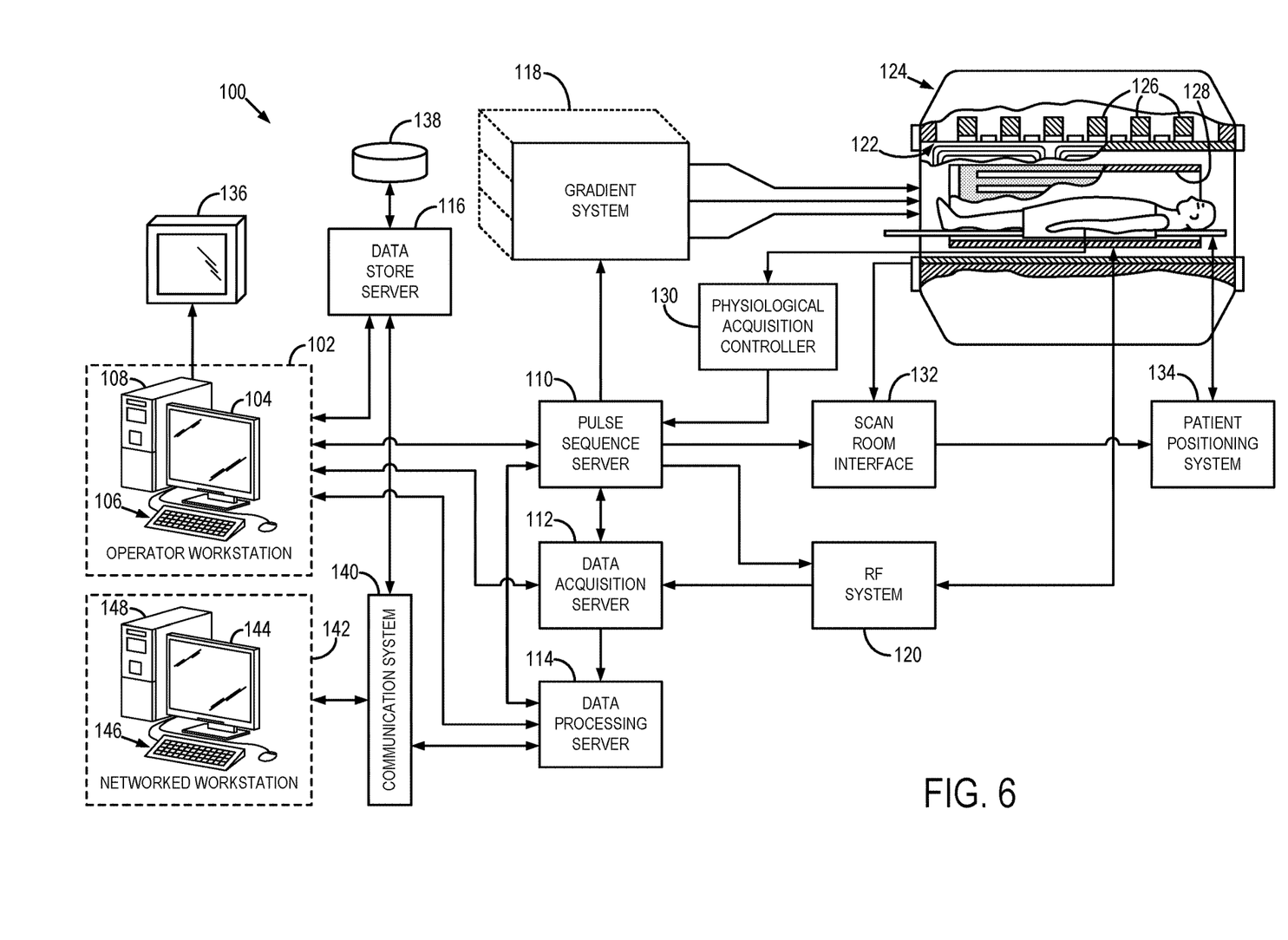
FIG. 6 is a block diagram of an example magnetic resonance imaging ("MRI") system that can be used to implement the methods described in the present disclosure.

Referring particularly now to FIG. 6, an example of an MRI system 100 that can implement the methods described here is illustrated. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{3};$$

and the phase of the received magnetic resonance signal may also be determined according to the following relationship:

$$\varphi = \tan^{-1}\left(\frac{Q}{I}\right). \tag{4}$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The systems and methods described herein can be particularly useful in areas where the wide B0 inhomogeneity is present along the extended field of view, which makes the collection of bSSFP based images challenging due to the persistent presence of banding artifacts. The phc-MRF technique described herein is capable of compensating for banding artifacts. This a fundamental step towards an MRF acquisition suitable for all body applications where a bSSFP based approach provides high SNR and ability to map tissue parameters and static field inhomogeneity.

The present disclosure has described one or more preferred embodiments, and it should be appreciated that many equivalents, alternatives, variations, and modifications, aside from those expressly stated, are possible and within the scope of the invention.

The invention claimed is:

1. A method for performing magnetic resonance fingerprinting (MRF) comprising:
    performing a balanced steady-state free precession (bSSFP) pulse sequence multiple times to acquire a multiple MRF datasets from at region of interest (ROI) in a subject, wherein performing the multiple bSSFP pulse sequences includes cycling through multiple phase patterns that differ across the multiple times;
    comparing the multiple MRF datasets with at least one MRF dictionary to determine at least one tissue property indicated by each of the multiple MRF datasets;
    producing an aggregated indication of the at least one tissue property; and
    producing at least one map of the at least one tissue property using the aggregated indication of the at least one tissue property.

2. The method of claim 1 wherein cycling through multiple phase patterns that differ across the multiple times includes performing a linear phase cycling with a phase increment ($\Delta\varphi$) for each timepoint of $\pi$, 0, $\pi/2$ and $3\pi/2$ of the multiple times.

3. The method of claim 1 wherein comparing the multiple MRF datasets with the at least one MRF dictionary includes comparing with a plurality of different dictionaries that are paired, one each, with the multiple MRF datasets.

4. The method of claim 1 wherein comparing the multiple MRF datasets with the MRF dictionary includes comparing each of the MRF datasets with a respective MRF dictionary to generate a respective inner product.

5. The method of claim 1 wherein aggregating the indication of the at least one tissue property includes producing an average of the at least one tissue property determined for each of the multiple MRF datasets.

6. The method of claim 1 further comprising performing a search across the aggregated indication of the at least one tissue property to determine a maximum value of the at least one tissue property.

7. The method of claim 1 wherein the at least one map of the at least one tissue property includes at least one of a T1 map, a T2 map, and a B0 map.

8. The method of claim 1 wherein the ROI in the subject is characterized by an inhomogeneous magnetic field.

9. A system comprising:
    a magnet system configured to generate a polarizing magnetic field about at least a portion of a subject;
    a magnetic gradient system including a plurality of magnetic gradient coils configured to apply at least one magnetic gradient field to the polarizing magnetic field;
    a radio frequency (RF) system configured to apply an RF field to the subject and to receive magnetic resonance signals from the subject using a coil array;
    a computer system programmed to:
        control the magnetic gradient system and the RF system to perform a balanced steady-state free precession (bSSFP) pulse sequence multiple times to acquire a multiple MRF datasets from at region of interest (ROI) in a subject, wherein performing the multiple bSSFP pulse sequences includes cycling through multiple phase patterns that differ across the multiple times;
        compare the multiple MRF datasets with a MRF dictionary to determine at least one tissue property indicated by each of the multiple MRF datasets;
        produce an aggregated indication of the at least one tissue property; and
        produce at least one map of the at least one tissue property using the aggregated indication of the at least one tissue property.

10. The system of claim 9 wherein the computer system is further programmed to cycle through multiple phase patterns that differ across the multiple times by performing a linear phase cycling with a phase increment ($\Delta\varphi$) for each timepoint of $\pi$, 0, $\pi/2$ and $3\pi/2$ of the multiple times.

11. The system of claim 9 wherein the computer system is further programmed utilize a plurality of different dictionaries that are paired, one each, with the multiple MRF datasets to compare the multiple MRF datasets with the at least one MRF dictionary.

12. The system of claim 9 wherein the computer system is further programmed to compare each of the MRF datasets with a respective MRF dictionary to generate a respective inner product when comparing the multiple MRF datasets with the MRF dictionary.

13. The system of claim 9 wherein the computer system is further programmed to produce an average of the at least one tissue property determined for each of the multiple MRF datasets to aggregate the indication of the at least one tissue property.

14. The system of claim 9 wherein the computer system is further programmed to perform a search across the aggregated indication of the at least one tissue property to determine a maximum value of the at least one tissue property.

15. The system of claim 9 wherein the at least one map of the at least one tissue property includes at least one of a T1 map, a T2 map, and a B0 map.

16. The system of claim 9 wherein the ROI in the subject is characterized by an inhomogeneous magnetic field.

* * * * *